United States Patent [19]
Bennett et al.

[11] Patent Number: 5,328,999
[45] Date of Patent: Jul. 12, 1994

[54] ENDO-1,4-β-GLUCANASE GENES AND THEIR USE IN PLANTS

[75] Inventors: Alan B. Bennett, Davis; Robert L. Fischer, El Cerrito; Coralie Lashbrook, Dixon, all of Calif.; James Giovannoni, Ithaca, N.Y.;

[73] Assignee: The Regents of the University of California, Oakland, Calif.

[21] Appl. No.: 687,466

[22] Filed: Apr. 18, 1991

Related U.S. Application Data

[63] Continuation-in-part of Ser. No. 511,417, Apr. 20, 1990, Pat. No. 5,168,064.

[51] Int. Cl.$^5$ .................. C07H 15/12; C12N 15/00; C12N 5/00; C12N 9/42
[52] U.S. Cl. .................. 536/24.5; 536/23.2; 536/23.6; 536/24.1; 435/172.3; 435/240.4; 435/320.1; 435/209
[58] Field of Search .................. 435/172.3, 209, 320.1, 435/240.4; 536/27, 23.2, 23.6, 24.1, 24.5; 800/205, DIG. 44

[56] References Cited

U.S. PATENT DOCUMENTS 5,801,540 1/1989 Hiatt et al. .................. 435/172.3

FOREIGN PATENT DOCUMENTS 0240208 10/1987 European Pat. Off. ...... C12N 15/00
0271988 6/1988 European Pat. Off. ...... C12N 15/00

OTHER PUBLICATIONS

Giovannoni et al. 1989. The Plant Cell 1(1):53–63.
Chang et al. 1985. Mol. Cell. Biol. 5(9):2341–2348.
Tigchelaar, E. C., et al., "Genetic Regulation of Tomato Fruit Ripening", *Hortic. Sci.*, 13:508–513 (1978).
Smith, C. J. S., et al., "Antisense RNA inhibition of polygalacturonase gene expression in transgenic tomatoes", *Nature*, 344:724–726 (1988).
Sheehy, R. E., et al., "Reduction of polygalacturonase activity in tomato fruit by antisense RNA," *Proc. Nat. Acad. Sci.*, 85:8805–8809 (1988).
Smith, C. J. S., et al., "Inheritance and effect on ripening of antisense polygalacturonase genes in transgenic tomatoes" *Plant Molecular Biology*, 14:369–379 (1990).
Hatfield, R., and Nevins, D. J., "Characterization of the Hydrolytic Activity of Avocado Cellulase", *Plant Cell Physiol.*, 27(3):541–552 (1986).
Christoffersen, R. E., et al., "Cellulase gene expression in ripening avocado fruit: The accumulaton of cellulase mRNA and protein as demonstrated by cDNA hybridizaton and immunodetection", *Plant Molecular Biol.*, 3:385–391 (1984).
Tucker, M. L., et al., "Bean Abscission Cellulase", *Plant Physiol.*, 88:1257–1262 (1988).
Sobotka, F. E. and Watada, A. E., "Cellulase in High Pigment and Crimson Tomato Fruit", *J. Amer. Soc. Hort. Sci.* 96(6):705–707 (1971).
Bennett, A. L. and Christoffersen, R. E., "Synthesis and Processing of Cellulase from Ripening Avacado Fruit," *Plant Physiol.* 81:830–835 (1986).

*Primary Examiner*—David T. Fox
*Attorney, Agent, or Firm*—Townsend and Townsend Khourie and Crew

[57] ABSTRACT

The present invention provides a method for reducing fruit softening and cell wall polysaccharide degradation by inhibiting endo-1,4-β-glucanase activity using antisense DNA constructs.

7 Claims, 8 Drawing Sheets

ATAAACATAA TATTAAATAG TCATAAACCA TATGTTAAAT AATAATAATA ATTAATTAAT

AATAACAAT ATG GCT TGT TCA AAG AAT ATT TGG GTT ATT GTT ATA TTC
         Met Ala Cys Ser Lys Asn Ile Trp Val Ile Val Ile Phe
         1                   5                   10

TTT TTG TGC ATT TTG GCT GGT CCT ATT ATT GCT CAA GAT TAC AAT GAT
Phe Leu Cys Ile Leu Ala Gly Pro Ile Ile Ala Gln Asp Tyr Asn Asp
            15                  20                  25

TCA CTT GGC AAA GCT ATT TTA TTC TTT GAA GGG CAA CGT TCT GGA AAA
Ser Leu Gly Lys Ala Ile Leu Phe Phe Glu Gly Gln Arg Ser Gly Lys
30                  35                  40                  45

TTA CCA GTT TCT CAA AGA GTC AAA TGG AGA GGA GAT TCC GCA CTC ATC
Leu Pro Val Ser Gln Arg Val Lys Trp Arg Gly Asp Ser Ala Leu Ile
            50                  55                  60

FIG. 2A.

```
GAT GGC ATA ATT GAA CAT GTG AAT TTG ATT GGA GGC TAC TAT GAT GCT
Asp Gly Ile Ile Glu His Val Asn Leu Ile Gly Gly Tyr Tyr Asp Ala
        65                      70                  75

GGT GAC AAT GTA AAA TTT GGA TGG CCC ATG GCT TAT TCT TTA ACC TTG
Gly Asp Asn Val Lys Phe Gly Trp Pro Met Ala Tyr Ser Leu Thr Leu
        80                      85                  90

TTG AGT TGG GCT GCT ATT GAA TAT CAA ACA CAA ATC TCT TCA ACA AAT
Leu Ser Trp Ala Ala Ile Glu Tyr Gln Thr Gln Ile Ser Ser Thr Asn
        95                      100                 105

CAA CTT GTA CAC CTC CAA AAT GCA ATT CGT TGG GGC ACA AAT TTC TTA
Gln Leu Val His Leu Gln Asn Ala Ile Arg Trp Gly Thr Asn Phe Leu
        110                     115                 120         125

ATT CGA GCC CAT ACT TCA AGT ACA ACT CTC TAT ACT CAG GTT GGA GAT
Ile Arg Ala His Thr Ser Ser Thr Thr Leu Tyr Thr Gln Val Gly Asp
        130                     135                 140
```

FIG. 2B.

GGA AAT GCA GAT CAC CAA TGT TGG GAA AGA CCA GAA GAC ATG GAT ACT
Gly Asn Ala Asp His Gln Cys Trp Glu Arg Pro Glu Asp Met Asp Thr
            145                     150                     155

CCT AGA ACA CTA TAT AAA ATA ACA TCA AAT TCT CCA GGA TCT GAG GTG
Pro Arg Thr Leu Tyr Lys Ile Thr Ser Asn Ser Pro Gly Ser Glu Val
            160                     165                     170

GCA GCT GAC GTG GCA GCT GCT TTT GCT GCT TCA ATA GTT TTC AAA
Ala Ala Asp Val Ala Ala Ala Phe Ala Ala Ala Ser Ile Val Phe Lys
            175                     180                     185

AAT ATT GAT TCC AAC TAT TCT ACA AAG TTA TTA AAA AGA TCA AGA TCC
Asn Ile Asp Ser Asn Tyr Ser Thr Lys Leu Leu Lys Arg Ser Arg Ser
            190                     195                     200                 205

TTA TTT GCA TTT GCG GAT AAG TAT AGA GGA TCT TAC CAA GCT TCT TGT
Leu Phe Ala Phe Ala Asp Lys Tyr Arg Gly Ser Tyr Gln Ala Ser Cys
            210                     215                     220

FIG. 2C.

CCA TTC TAT TGT TCC TAC TCA GGT TAT AAG GAT GAA TTG TTG TGG GCT
Pro Phe Tyr Cys Ser Tyr Ser Gly Tyr Lys Asp Glu Leu Leu Trp Ala
225                         230                         235

GCT GCT TGG CTA TAT AAG GCA GGT GGA AAC AAT TAT TTA AAT TAT
Ala Ala Trp Leu Tyr Lys Ala Gly Gly Asn Asn Tyr Leu Asn Tyr
240                         245                         250

GCT TCA ATC AAC CAA GGT TGG AGT CAA GTT GCC TCT GAG TTT AGT TGG
Ala Ser Ile Asn Gln Gly Trp Ser Gln Val Ala Ser Glu Phe Ser Trp
255                         260                         265

GAT GAC AAG TTT GCT GGA GCC CAA ACT TTA CTA GCT AAG GAA TAC CTT
Asp Asp Lys Phe Ala Gly Ala Gln Thr Leu Leu Ala Lys Glu Tyr Leu
270                         275                         280                         285

AAT GGA AAG AGC AAT TTG GAA AAA TTC AAG AAA GAT GCT GAT TCA TTT
Asn Gly Lys Ser Asn Leu Glu Lys Phe Lys Lys Asp Ala Asp Ser Phe
290                         295                         300

FIG. 2D.

```
ATT TGT GGA TTA ATG CCA GAA AGT AGC TCT ATA CAA ATT AAG ACA ACC
Ile Cys Gly Leu Met Pro Glu Ser Ser Ser Ile Gln Ile Lys Thr Thr
        305                 310                 315

CCA GGT GGA CTT TTG TAT TAT AGA GAT AGT AGC AAT TTG CAA TAT GTG
Pro Gly Gly Leu Leu Tyr Tyr Arg Asp Ser Ser Asn Leu Gln Tyr Val
        320                 325                 330

AAT GGT GCC ACT ATG GTA CTT TTT ATG TAC ACT AAA GTC CTT GAG GCA
Asn Gly Ala Thr Met Val Leu Phe Met Tyr Thr Lys Val Leu Glu Ala
        335                 340                 345

GCT GGA ATA GGA GGA GTT ACA TGT GGA TCT GTT AAT TTT TCC ACA TCC
Ala Gly Ile Gly Gly Val Thr Cys Gly Ser Val Asn Phe Ser Thr Ser
        350                 355                 360                 365

AAG ATT AAA GCC TTT GCA AAA TTA CAG GTT GAC TAC ATA CTT GGA AAC
Lys Ile Lys Ala Phe Ala Lys Leu Gln Val Asp Tyr Ile Leu Gly Asn
        370                 375                 380
```

*FIG. 2E.*

AAT CCA CTC AAA ATG TCA TAC ATG GTG GGA TTT GGC AAC AAA TAT CCA
Asn Pro Leu Lys Met Ser Tyr Met Val Gly Phe Gly Asn Lys Tyr Pro
              385                 390                 395

ACA AAA CTT CAC CAT AGA GCC TCA CTC CCT TCA ATT TAT AAC CAT
Thr Lys Leu His His Arg Ala Ser Leu Pro Ser Ile Tyr Asn His
        400                 405                 410

CCA ACT AGG GTG GGG TGC AAC GAT GGC TAT AGT TCA TGG TAC AAT TCT
Pro Thr Arg Val Gly Cys Asn Asp Gly Tyr Ser Ser Trp Tyr Asn Ser
              415                 420                 425

AAC AAT CCA AAC ACA CAT GTC GGT GCG ATC GTC GGT GGG CCT
Asn Asn Pro Asn Thr His Val Gly Ala Ile Val Gly Gly Pro
          430                 435                 440                 445

AAT TCC GGG GAC CAA TTT ATT GAT TCG CGA TCA GAT TAC TCT CAT TCT
Asn Ser Gly Asp Gln Phe Ile Asp Ser Arg Ser Asp Tyr Ser His Ser
              450                 455                 460

FIG. 2F.

GAA CCC ACG ACT TAT ATG AAT GCA GCA TTT ATA GGG TCC GTG GCC GCT
Glu Pro Thr Thr Tyr Met Asn Ala Ala Phe Ile Gly Ser Val Ala Ala
        465                          470                      475

TTG ATT GAT CAA ACC AAA GAA GGA GAA CAC TAT GGG GAA ATT AAT TCA
Leu Ile Asp Gln Thr Lys Glu Gly Glu His Tyr Gly Glu Ile Asn Ser
        480                          485                      490

CAA TTT AAC AAA ACA GGT TTT ATG TAG T AGATAAATTA GTAAAGAAGT
Gln Phe Asn Lys Thr Gly Phe Met *
        495                  500

GAATGTCATG CAATTATTGA TAAATATATG TACATATAAT GAATTATCAT AAATGTATGA

AGCTATAAAT ATTACATAAT AGAAATAAAT AAATATCAAA AATGTATCTT TTTTTTTTTT

ENDO-1,4-β-GLUCANASE GENES AND THEIR USE IN PLANTS

This invention was made with Government support under Grant Nos. CRCR-87-1-2525 and CRCR-87-1-2526 awarded by the U.S. Department of Agriculture. The Government has certain rights in this invention.

RELATED APPLICATION

This application is a continuation-in-part of U.S. patent application Ser. No. 07/511,417, filed Apr. 20, 1990, now U.S. Pat. No. 5,168,064, the entire disclosure of which is incorporated herein by reference.

BACKGROUND OF THE INVENTION

1. Field of the Invention

The present invention relates generally to methods for reducing fruit softening. In particular, it relates to methods for reducing fruit softening and cell wall polysaccharide degradation by inhibiting the activity of one or more endo-1,4-β-glucanase 2. Information Disclosure Ripening, the final phase of fruit development, involves a number of dramatic metabolic changes in fruit tissue. An important aspect of the ripening process is fruit softening, which is thought to result primarily from modifications of the cell wall. Many subtle changes in metabolic activity are involved in this response.

The prior art discloses ripening-impaired mutants, such as the rin mutant which have been used to study fruit ripening. Tigchelaar *Hortic. Sci.*, 13:508–513, 1978. The use of these mutants to specifically control fruit softening has met with limited success, however, because of the pleiotropic nature of these mutations.

An increase in the activity of polygalacturonase, an enzyme responsible for the degradation of pectin, has been correlated with fruit softening. Recombinant constructs have been prepared containing a plant promoter linked to polygalacturonase cDNA in the antisense direction. These constructs have been inserted into tomato to inhibit the activity of this enzyme in ripening fruit. Smith et al., *Nature*, 334:724–726, 1988; Sheehy et al., *Proc. Nat. Acad. Sci.*, 85:8805–8809, 1988; Hiatt et al., U.S. Pat. No. 4,801,340; Bridges et al., EPO Publication No. 0,271,988. Although these constructs have been shown to inhibit polygalacturonase activity, an effect on fruit softening has not been shown. Smith et al.,*Plant Mol.* 14:369–379, 1990.

Endo-1,4-β-glucanase is another enzyme thought to be involved in fruit softening. It is known to degrade the major hemicellulosic polymer, xyloglucan. Hatfield and Nevins, *Plant and Cell Physiol.*, 27:541–552, 1986. The cDNA and gene encoding endo-1,4-β-glucanase have been cloned from avocado (Christoffersen et al., *Plant Molec. Biol.*, 3:385, 1984) and bean (Tucker et al., *Plant Physiol.*, 88:1257, 1988), both of which are incorporated herein by reference.

SUMMARY OF THE INVENTION

The present invention relates to methods of reducing fruit softening and inhibiting the degradation of cell wall polymers comprising, introducing into a plant an expression cassette having a plant promoter sequence operably linked to a DNA subsequence of at least 20 base pairs derived from a DNA sequence encoding an endo-1,4-β-glucanase, the DNA subsequence being linked to the promoter sequence in the opposite orientation for expression (i.e., in the antisense direction). The promoter can be either inducible or constitutive. If inducible, it is preferably derived from the tomato E8 gene. If constitutive, it is preferably the 35S promoter of cauliflower mosaic virus.

The method can be modified by using an expression cassette as described above plus a second expression cassette having a plant promoter sequence operably linked to a subsequence of at least 20 base pairs derived from a gene encoding a second glucanase or a polygalacturonase. The other DNA sequences are also linked to the promoter sequence in the opposite orientation for expression.

Economically important crop plants suitable for the method include tomato and pepper. The expression cassette can be introduced into the plant by any in vitro technique, preferably using Agrobacterium. The expression cassette can also be introduced into the plant by a sexual cross.

The present invention also provides a method of inhibiting the activity of an endo-1,4-β-glucanase comprising, introducing into a plant an expression cassette having a plant promoter sequence operably linked to a DNA subsequence of at least 20 base pairs derived from a DNA sequence encoding the endo-1,4-β-glucanase, the DNA subsequence being linked to the promoter sequence in the opposite orientation for expression. By inhibiting the enzyme, cell wall polysaccharide degradation can be inhibited.

The present invention further provides an expression cassette comprising a plant promoter sequence operably linked to a DNA subsequence of at least 20 base pairs derived from a DNA sequence encoding endo-1,4-β-glucanase, the DNA subsequence being linked to the promoter sequence in the opposite orientation for expression. The promoter can be inducible, typically the E8 promoter, or constitutive, typically derived from cauliflower mosaic virus.

A plant, preferably tomato, is also provided that contains an expression cassette having a plant promoter sequence operably linked to a DNA subsequence of at least 20 base pairs derived from a DNA sequence encoding an endo-1,4-β-glucanase, the DNA subsequence being linked to the promoter sequence in the opposite orientation for expression.

The present invention further provides a DNA sequence which is uninterrupted, which encodes an endo-1,4-β-glucanase, and which is flanked on at least one side by non-wild type DNA. The DNA sequence is typically a cDNA sequence derived from tomato.

Further, an expression cassette is provided which comprises a promoter sequence operably linked to a DNA sequence which is uninterrupted and which encodes an endo-1,4-β-glucanase. The DNA sequence is typically a cDNA sequence derived from tomato. The promoter sequence function in both prokaryotes and eukaryotes.

The present invention also provides a method of isolating from a plant a DNA sequence encoding an endo-1,4-β-glucanase comprising, probing a DNA library prepared from plant tissue with oligonucleotide probes comprising a conserved sequence from endo-1,4-β-glucanase cDNA. The DNA library can be either a genomic or cDNA library. The preferred conserved sequences are:

```
5' TCCATATCTTCIGGICGTTCCCAACA 3'   and
       G  C      C     G

5' TTATCICCIGCATCATAATAICCICC 3'
      G       G G G
```

Finally, a DNA construct is provided comprising a promoter sequence operably linked to a DNA sequence encoding a signal peptide from a tomato endo-1,4-β-glucanase, the DNA sequence being joined to other than a sequence encoding mature tomato endo-1,4-β-glucanase.

BRIEF DESCRIPTION OF THE DRAWINGS

FIGS. 2A-2G present the nucleotide sequence of the +cl1 cDNA and the amino acid sequence of the protein encoded by it.

DESCRIPTION OF THE PREFERRED EMBODIMENTS

Figure 1:
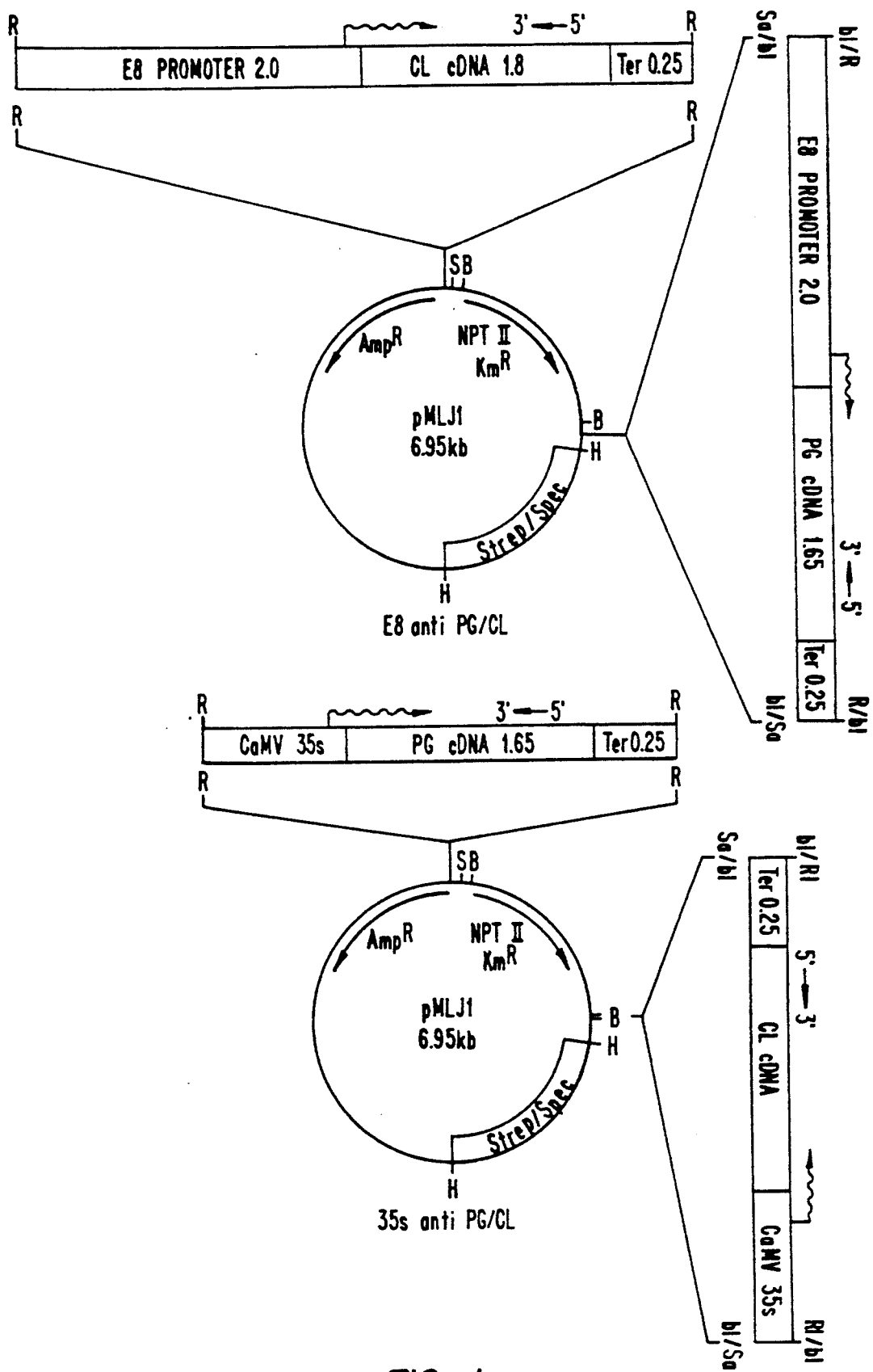
FIG. 1 illustrates the construction of the pMLJ1:E8antiPG/CL and pMLJ1:CamVantiPG/CL vectors.

An improved method of reducing fruit softening in various agronomically important plant species is provided. The method comprises transforming a plant cell with an expression cassette having a plant promoter operably linked to an endo-1,4-β-glucanase (glucanase) DNA in the opposite orientation for normal expression. Expression cassettes which comprise other glucanase DNAs and/or polygalacturonase DNAs in the antisense direction can also be used. The glucanase cDNAs can also be inserted in correct orientation for expression of the genes in plant or bacterial cells. Also provided are nucleic acid probes comprising conserved regions of the endo-1,4-β-glucanase genes which can be used to isolate other genes from the same or different plant species. The cDNA sequences provided by this invention can be used to construct vectors capable of expressing fusion proteins comprised of the glucanase signal peptide fused to any foreign gene. This provides for the secretion of foreign gene products from the plant cell.

Control of the rate of fruit softening during the ripening process is of tremendous economic importance. In the case of tomatoes, inhibition of fruit softening allows fresh market tomatoes to remain firm while ripening on the vine. Vine ripened tomatoes have better flavor and color development then those that are picked while green. Control of fruit ripening may also improve fruit quality by increasing pathogen resistance. These properties allow for longer shelf and shipping life of the tomato fruit. Inhibition of cell wall degradation may also enhance the processing characteristics of the tomato fruit by increasing fruit viscosity and consistency.

The present invention provides a method for reducing fruit softening by inhibiting the activity of one or more glucanases in various agronomically important species. In the exemplified case, cDNA from tomato glucanase genes is used to create expression cassettes comprising antisense DNA to control the activity of the gene during fruit ripening.

Recombinant DNA techniques are used to introduce the antisense cDNA sequences into a suitable vector which is subsequently used to transform a suitable host cell. In the exemplified case, *Agrobacterium tumefaciens* is used as a vehicle for transmission of the cDNA to the ultimate host, the tomato cell. A plant regenerated from the transformed cell transcribes the antisense cDNAs which inhibit activity of the enzyme. In plant cells, it has been shown that cDNA inhibits gene expression by preventing the accumulation of mRNA which results in decreased levels of the protein encoded by the gene. Sheehy et al., supra.

The following descriptions will detail various methods available to introduce and express foreign DNA sequences in plant cells. Specific examples of preferred methods are also described.

In summary, the manipulations necessary to prepare antisense glucanase cDNAs and introduce them into a plant cell involve 1) isolating mRNA from ripe fruit, 2) preparing cDNA from the mRNA, 3) screening the cDNA for the desired sequences, 4) linking a plant promoter to the desired cDNAs in the opposite orientation for expression of the glucanase genes, 5) transforming suitable host plant cells, and 6) selecting and regenerating cells which transcribe the inverted sequences.

I. General Methods

Generally, the nomenclature used hereafter and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., 1989. The manual is hereinafter referred to as "Sambrook". Other general references are provided throughout this document. The procedures therein are believed to be well known in the art and are provided for the convenience of the reader. All the information contained therein is incorporated herein by reference.

II. Preparation of endo-1,4-β-glucanase cDNA

To prepare cDNA from various glucanase genes, mRNA from ripe fruit is first isolated. Eukaryotic mRNA has at its 3' end a string of adenine nucleotide residues known as the poly-A tail.

Short chains of oligo d-T nucleotides are then hybridized with the poly-A tails and serve as a primer for the enzyme reverse transcriptase. This enzyme uses RNA as a template to synthesize a complementary DNA (cDNA) strand. A second DNA strand is then synthesized using the first cDNA strand as a template. Linkers are added to the double-stranded cDNA for insertion into a plasmid or λ phage vector for propagation in *E. coli*.

Identification of clones harboring the desired cDNAs is performed by either nucleic acid hybridization or immunological detection of the encoded protein, if an expression vector is used. The bacterial colonies are then replica plated on nitrocellulose filters. The cells are then lysed and probed with either oligonucleotides complimentary to the desired cDNAs or with antibodies to the desired protein.

In the exemplified case described below, highly conserved regions found in both avacado and bean glucanases (see, Christoffersen et al., supra and Tucker et al., supra) were used to construct degenerate oligonucleotide probes to screen a tomato fruit cDNA library. Cross-hybridization experiments indicate that a family of glucanase genes is expressed during tomato fruit ripening. Three genes within the family were identified as tcl1, tcl2, and tcl3.

The nucleotide sequence of the tcl1 cDNA (Sequence No. 1) is provided in FIG. 1. The cDNA was deposited with the American Type Culture Collection, Rockville, Md. on Apr. 20, 1990 and has Accession No. 68312. Table 1 shows the nucleotide sequence of a portion of tcl2 cDNA (Sequence No.2). This sequence corresponds to nucleotides 319 to 423 in the tcl1 nucleotide sequence presented in FIG. 1. The sequences may be used in any of a number of ways. For instance, fragments of the sequences can be used as probes to identify other glucanase genes in genomic or cDNA libraries prepared from other plant species.

The cDNAs can be inserted in the antisense direction into expression cassettes to inhibit the expression of the glucanase gene in plant cells. The cDNA sequence, itself, can also be inserted in an expression cassette for expression in bacteria or plant cells. Insertion of the expression cassette in bacteria is useful for biomass conversion of plant tissues to ethanol or methanol.

The sequence provided can also be used for expression of fusion proteins comprised of a portion of the glucanase enzyme fused to another protein. Of particular interest is the transit peptide sequence of the protein. As is well known in the art, proteins transported across the cell membrane typically have an N-terminal sequence rich in hydrophobic amino acids about 15 to 30 amino acids long. Sometime during the process of passing through the membrane, the signal sequence is cleaved by signal peptidase. Watson et al., *Molecular Biology of the Gene*, p. 731, 1987. Thus, the signal peptide encoding sequence of a tomato endo-1,4-β-glucanase gene may be linked to another, foreign, structural gene to provide for transport of the foreign gene product to the cell wall. The foreign structural gene may be derived from any source including bacteria, yeast, animals or plants. Typically, the signal peptide encoding sequence will be joined at its 3' end to a linker for attachment to the foreign structural gene in the proper reading frame. Foreign genes of interest include carbohydrate and cell wall metabolizing enzymes, such as invertase, dextransucrase, levansucrase. Also of interest are genes that encode proteins involved in disease resistance such as chitinase, hydroxyprotein-rich glycoproteins, and polygalacturonase inhibiting proteins.

of the antisense cDNAs in plants. Companion sequences, of bacterial or viral origin, are also included to allow the vector to be cloned in a bacterial or phage host.

The vector will preferably contain a broad host range prokaryote origin of replication. A selectable marker should also be included to allow selection of bacterial cells bearing the desired construct. Suitable prokaryotic selectable markers include resistance to antibiotics such as kanamycin or tetracycline.

Other DNA sequences encoding additional functions may also be present in the vector, as is known in the art. For instance, in the case of Agrobacterium transformations, T-DNA sequences will also be included for subsequent transfer to plant chromosomes.

A bacterial expression vector may be used if expression of the glucanase cDNAs in bacteria is desired. Insertion of an expression vector into bacteria is useful in biomass conversion of plant tissues to ethanol or methanol. Construction of a bacterial expression vector is typically done by placing the cDNA downstream from a strong bacterial promoter Examples of bacterial promoters that might be used include β-lactamase, β-galactosidase, and the phage λpL promoters. The efficiency of translation of mRNA in bacteria is critically dependent on the presence of a ribosome-binding site and its distance from the transcription initiation codon.

For expression in plants, the recombinant expression cassette will contain in addition to the desired sequence, a plant promoter region, a transcription initiation site (if the sequence to be transcribed lacks one), and a transcription termination sequence. Unique restriction enzyme sites at the 5' and 3' ends of the cassette are typically included to allow for easy insertion into a pre-existing vector.

Sequences controlling eukaryotic gene expression have been extensively studied. Promoter sequence elements include the TATA box consensus sequence (TATAAT), which is usually 20 to 30 base pairs (bp) upstream of the transcription start site. In most instances the TATA box is required for accurate transcription initiation. By convention, the start site is called +1. Sequences extending in the 5' (upstream) direction are given negative numbers and sequences extending in the 3' (downstream) direction are given positive numbers.

In plants, further upstream from the TATA box, at positions −80 to −100, there is typically a promoter element with a series of adenines surrounding the trinucleotide G (or T) N G. J. Messing et al., in *Genetic Engineering in Plants*, pp. 221–227 (Kosage, Meredith and Hollaender, eds. 1983). Other sequences conferring

TABLE 1

```
                30                                             60
GTT TTT CCG ATG GCG TTT ACG ACG ACA TTG TTA TCG TGG AGT ATA ATT GAT TTT AAA AGG
 V   F   P   M   A   F   T   T   T   L   L   S   W   S   I   I   D   F   K   R 90                                            120
AAT ATA GGG AAT GAA TTG GGT AAT GCA GTG AAG GCG GTG AAA TGG GGA ACT GAT TTT CTG
 N   I   G   N   E   L   G   N   A   V   K   A   V   K   W   G   T   D   F   L 150                                            180
TTG AAA GCT ACG GCG AGA GAT GGA GTG ATA TAT GTA CAA GTT GGT GAT GCG TTT TCA GAT
 L   K   A   T   A   R   D   G   V   I   Y   V   Q   V   G   D   A   F   S   D

CAC AGT TGT TGG GAG AGA CCA GAG A
 H   S   C   W   E   R   P   E
```

III. Vector construction

The desired recombinant vector will comprise an expression cassette designed for initiating transcription tissue specificity, response to environmental signals, or maximum efficiency of transcription may also be found in the promoter region. Such sequences are often found within 400 bp of transcription initiation size, but may extend as far as 2000 bp or more.

In the construction of heterologous promoter/structural gene combinations, the promoter is preferably positioned about the same distance from the heterologous transcription start site as it is from the transcription start site in its natural setting. As is known in the art, however, some variation in this distance can be accommodated without loss of promoter function.

The particular promoter used in the expression cassette is a noncritical aspect of the invention. Any of a number of promoters which direct transcription in plant cells is suitable. The promoter can be either constitutive or inducible. Promoters of bacterial origin include the octopine synthase promoter, the nopaline synthase promoter and other promoters derived from native Ti plasmids. Herrara-Estrella et al., *Nature*, 303:209-213, 1983. Viral promoters include the 35S and 19S RNA promoters of cauliflower mosaic virus. Odell et al. *Nature*, 313:810-812, 1985. Possible plant promoters include the ribulose-1,3-bisphosphate carboxylase small subunit promoter and the phaseolin promoter. The promoter sequence from the E8 gene and other genes in which expression is induced by ethylene may also be used. The isolation and sequence of the E8 promoter is described in detail in Deikman and Fischer, *EMBO J.* 7:3315-3327, 1988. which is incorporated herein by reference.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Alber and Kawasaki, *Mol. and Appl. Genet*, 1:419-434, 1982. Polyadenylation is of importance for expression of the glucanase cDNA in plant cells. Polyadenylation sequences include, but are not limited to the Agrobacterium octopine synthase signal (Gielen et al., *EMBO J.*, 3:835-846, 1984) or the nopaline synthase signal (Depicker et al., *Mol. and Appl. Genet*, 1:561-573, 1982).

The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow in a medium containing the particular antibiotic.

IV. Transcription of endo-1,4-$\beta$-glucanase antisense cDNA in plant cells

A. Transformation of plant cells by in vitro techniques

1. Direct Transformation

The vector described above can be microinjected directly into plant cells by use of micropipettes to mechanically transfer the recombinant DNA. Crossway, *Mol. Gen. Genetics*, 202:179-185, 1985. The genetic material may also be transferred into the plant cell using polyethylene glycol, Krens, et al., *Nature*, 296, 72-74, 1982.

Another method of introduction of nucleic acid segments is high velocity ballistic penetration by small particles with the nucleic acid either within the matrix of small beads or particles, or on the surface, Klein, et al., *Nature*, 327, 70-73, 1987.

Yet another method of introduction is fusion of protoplasts with other entities, either minicells, cells, lysosomes or other fusible lipid-surfaced bodies, Fraley, et al., *Proc. Natl. Acad. Sci. U.S.A.*, 79, 1859-1863, 1982.

The DNA may also be introduced into the plant cells by electroporation. Fromm et al., *Pro Natl Acad Sci U.S.A.*, 82:5824 (1985). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

2 Vectored Transformation

Cauliflower mosaic virus (CaMV) may be used as a vector for introducing the antisense DNA into plant cells. (Hohn et al , 1982 "*Molecular Biology of Plant Tumors,*" Academic Press, New York, pp.549-560; Howell, U.S. Pat. No. 4,407,956). In accordance with the described method, the entire CaMV viral DNA genome is inserted into a parent bacterial plasmid creating a recombinant DNA molecule which can be propagated in bacteria. After cloning, the recombinant plasmid is further modified by introduction of the desired sequence into unique restriction sites in the viral portion of the plasmid. The modified viral portion of the recombinant plasmid is then excised from the parent bacterial plasmid, and used to inoculate the plant cells or plants.

Another method of introducing the DNA into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants.

Agrobacterium is a representative genus of the gram-negative family Rhizobiaceae. Its species are responsible for crown gall (*A. tumefaciens*) and hairy root disease (*A. rhizogenes*) The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome. J. Schell, *Science*, 237:1176-1183, 1987.

Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid. Hoekema, et al , *Nature*, 303:179-189, 1983. The transferred DNA region, can be increased in size by the insertion of heterologous DNA without its ability to be transferred being affected. A modified Ti or Ri plasmid, in which the disease-causing genes have been deleted, can be used as a vector for the transfer of the gene constructs of this invention into an appropriate plant cell.

Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to "shuttle vectors", (Ruvkun and Ausubel, 1981, *Nature* 298:85–88), promoters, (Lawton et al., 1987, *Plant Mol. Biol.* 9:315–324) and structural genes for antibiotic resistance as a selection factor (Fraley et al., *Proc. Nat. Acad. Sci,* 80:4803–4807, 1983).

All plant cells which can be transformed by Agrobacterium and from which whole plants can be regenerated can be transformed according to the present invention to produce transformed intact plants which contain the desired DNA. There are two common ways to transform plant cells with Agrobacterium:

(1) co-cultivation of Agrobacterium with cultured isolated protoplasts, or (2) transformation of intact cells or tissues with Agrobacterium.

Method (1) requires an established culture system that allows for culturing protoplasts and subsequent plant regeneration from cultured protoplasts.

Method (2) requires (a) that the intact plant tissues, such as cotyledons, can be transformed by Agrobacterium and (b) that the transformed cells or tissues can be induced to regenerate into whole plants.

Most dicot species can be transformed by Agrobacterium. All species which are a natural plant host for Agrobacterium are transformable in vitro. Monocotyledonous plants, and in particular, cereals, are not natural hosts to Agrobacterium. Attempts to transform them using Agrobacterium have been unsuccessful until recently. Hooykas-Van Slogteren et al., *Nature,* 311:763–764, 1984. There is growing evidence now that certain monocots can be transformed by Agrobacterium. Using novel experimental approaches cereal species such as rye (de la Pena et al., *Nature* 325:274–276, 1987), corn (Rhodes et al., *Science* 240:204–207, 1988), and rice (Shimamoto et al., *Nature* 338:274–276, 1989) may now be transformed.

B. Selection and Regeneration of transformed plant cells

After transformation, transformed plant cells or plants comprising the antisense DNA must be identified. A selectable marker, such as those discussed, supra, is typically used. Transformed plant cells can be selected by growing the cells on growth medium containing the appropriate antibiotic. The presence of opines can also be used if the plants are transformed with Agrobacterium.

After selecting the transformed cells, one can confirm expression of the desired heterologous gene. Simple detection of mRNA encoded by the inserted DNA can be achieved by well known methods in the art, such as Northern blot hybridization. The inserted sequence can be identified by Southern blot hybridization, as well. See, e.g., Sambrook, supra.

After determination of the presence of the antisense DNA, whole plant regeneration is desired. All plants from which protoplasts can be isolated and cultured to give whole regenerated plants can be transformed by the present invention. Some suitable plants include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, Malus, Apium, and Datura.

Plant regeneration from cultured protoplasts is described in Evans et al., *Handbook of Plant Cell Cultures,* Vol. 1: (MacMillan Publishing Co. New York, 1983); and Vasil I. R. (ed.), *Cell Culture and Somatic Cell Genetics of Plants,* Acad. Press, Orlando, Vol. I, 1984, and Vol. III, 1986.

It is known that practically all plants can be regenerated from cultured cells or tissues, including but not limited to, all major species of sugarcane, sugar beet, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

V. Definitions

The terms "endo-1,4-$\beta$-glucanase" or "glucanase" refer to a member of the class of plant enzymes capable of cleaving $\beta$-1,4 glucan linkages and degrading carboxymethylcellulose. These enzymes do not degrade crystalline cellulose and are thus distinguishable from certain bacterial cellulases. The class may be identified in that each member contains a highly conserved region which is substantially homologous to the amino sequences GGYYDAGDN or CWERPEDMD.

Each plant species contains a family of glucanase heteroallelic genes. The genes in the glucanase family are identifiable by, for example, their nucleotide sequence, the temporal pattern of their expression and the tissues in which they are expressed. Typically, expression of the glucanase genes of the present invention (as measured by, for instance, mRNA levels) generally follows the development of ripening fruit.

The phrase "DNA sequence" refers to a single or double-stranded polymer of deoxyribonucleotide bases read from the 5' to the 3' end. It includes both selfreplicating plasmids, infectious polymers of DNA and non-functional DNA.

The term "promoter" refers to a region of DNA upstream from the structural gene and involved in recognition and binding RNA polymerase and other proteins to initiate transcription. A "plant promoter" is a promoter capable of initiating transcription in plant cells.

The term "plant" includes whole plants, plant organs (e.g., leaves, stems, roots, etc.), seeds and plant cells.

The phrase "suitable host" refers to a microorganism or cell that is compatible with a recombinant plasmid, DNA sequence or recombinant expression cassette and will permit the plasmid to replicate, to be incorporated into its genome, or to be expressed.

The term "expression" refers to the transcription and translation of a structural gene so that a protein is synthesized.

A "constitutive" promoter is a promoter which is active under most environmental conditions and states of development or cell differentiation.

An "inducible" promoter is a promoter which is under more precise environmental or developmental control. Examples of environmental conditions that may effect transcription by inducible promoters include anaerobic conditions or the presence of light. Examples of promoters under developmental control include promoters that initiate transcription only in certain tissues, such as the promoter from the E8 gene which is induced by ethylene in ripening fruit.

The term "opposite orientation for expression" refers to a double-stranded DNA sequence from a structural gene that is inserted in an expression cassette in an inverted manner with respect to its naturally occurring orientation. Specifically, the strand that is normally the "template strand becomes the coding strand, and vice versa.

The term "uninterrupted" refers to a DNA sequence containing an open reading frame that lacks intervening, untranslated sequences.

The term "non-wild type DNA" refers to DNA sequences that do not flank a given DNA sequence in its naturally occurring environment.

The following experimental results are offered by way of example and not by way of limitation.

EXAMPLE I

This example describes the isolation of glucanase cDNAs and the construction of antisense expression vectors suitable for transformation of plant cells. For purposes of illustration only, the exemplified vectors comprise tcl1 antisense DNA. It will be understood that other glucanase genes can also be used in the disclosed methods without significant modification.

A. Preparation of tomato endo-1,4-β-glucanase cDNA

1. cDNA Library Production

A vector-primed cDNA library was prepared using standard methods. The library was prepared in the cloning vector pARC7 from ripe tomato fruit poly-A RNA by the method of Alexander et al., Gene, 31:79-89, 1984, which is incorporated herein by reference.

2. cDNA Library Screening a. Growing Colonies

HB101 cells containing a red ripe tomato-derived cDNA library were titered and dilutions were made to give approximately 5000 colonies per 10 ml of Luria Broth (LB). Ten ml aliquots of chilled bacterial suspension were vacuum filtered onto ten 132 mm nitrocellulose filters, which were then placed colony sides up on LB-agar plates containing 100 ug/ml ampicillin. Plates were incubated at 37° C. until colonies were approximately 0.5 mm in diameter.

b. Replica Plating

Master filters were removed from plates, numbered and given orientation marks with black ink. A fresh filter was wetted on a fresh LB plate and was laid on top of each master filter and orientation marks copied to the replicate. This process of colony transfer was repeated with a 2nd fresh filter to give two replica filters per master filter. Replicates were grown on LB-agar plates at 37° C. until colonies were approximately 0.5 mm and then were transferred to plates containing LB-agar with 150 ug/ml chloramphenicol. These were grown 12 hours at 37° C.

c. Bacterial Colony Lysis

Replica filters were removed from plates and placed colony sides up at room temperature on sheets of Whatman 3 MM paper wetted with 0.5 M NaOH/1.5 M NaCl. After 10 minutes, filters were blotted on dry 3 MM paper and transferred for 2 minutes to 3 MM paper wetted with 1 M Tris pH 7/1.5 M NaCl. Filters were immersed in 3× SSC for 15 seconds, placed on dry 3 MM paper and air dried prior to baking at 80° C. under vacuum for 2 hours.

d. Hybridization to Oligonucleotide Probe

Bacterial debris was removed from baked filters by washing with 3× SSC/0.1% SDS at 62° C. for 24 hours, during which time wash solution was replaced with fresh solution 3 times. Filters were collectively prehybridized at 37° C. overnight with 6× SSC, 1× Denhardts Solution, 0.5% SDS, 0.05% NaPPi and 0.1 mg/ml boiled and ice-quenched salmon sperm DNA. The 20 filters were then divided into two groups of replicates for hybridization.

Two 26 base oligonucleotide probe were synthesized at a DNA synthesizing facility. Probe sequences corresponded to two regions of glucanase that are completely conserved at the amino acid level in bean abscission zone glucanase and avocado fruit glucanase. Oligonucleotides were solubilized in 10 mM Tris-EDTA (TE) pH 8 and extracted with TE-saturated butanol; they were then adjusted to 0.3M in ammonium acetate and were precipitated with 4 volumes of ethanol at −80° C. DNA was harvested by centrifugation and was brought to 1 mg/ml in TE pH 8.

One ug of each oligonucleotide probe was end labeled with 32P-ATP according to the T4 DNA Polymerase Labeling System (Bethesda Research Labs) protocol supplied by the manufacturer. Specific activity of each probe exceeded $5 \times 10^7$ cpm/ug.

Each set of replica filters was incubated overnight at 42° C. in a hybridization bag containing 15 ml of hybridization buffer and one of the boiled and ice-quenched radiolabeled probes. Hybridization medium was 6× SSC, 1× Denhardt's solution, 0.05% NaPPi and 0.1 mg/ml boiled and ice-quenched salmon sperm DNA.

Filters were washed at 42° C. in 6× SSC, 0.05% NaPPi for several hours with several buffer changes. They were then exposed to Kodak X-O-Mat AR film at −80° C. for 24 hours using an intensifying screen. Film was developed and clones containing glucanase probe sequence were identified via the comparison of orientation marks on the film with those on the corresponding master plate.

e. Secondary Screening of Putative Glucanase Clones

Colonies identified by the glucanase oligonucleotide probes were picked with sterile toothpicks, dispersed into 1 ml LB and incubated with shaking at 37° C. for 2.5 hours. Suspensions were then diluted 500,000-fold and vacuum filtered in 5 ml aliquots of chilled LB through 82 mm nitrocellulose filters. These were grown at 37° C. on LB agar with 100 ug/ml ampicillin for 8 hours prior to their transfer to LB agar plates containing 150 ug/ml chloramphenicol. These were then incubated at 37° C for 12 hours. Filters were processed and screened with radiolabeled oligonucleotides probes as per steps 3 and 4 above. Single colonies of each of the 28 glucanase clones identified in the secondary screen were picked into 3 ml of LB ampicillin and grown overnight at 37° C. Cross hybridization experiments revealed that the clones could be arranged in three distinct classes, tcl1, tcl2, and tcl3.

f. Southern Analysis of Glucanase Clones

Mini prep DNA was isolated from bacterial cultures by the method of Kraft et al. *Biotechniques* 6(6):544–546 which is incorporated herein by reference. DNA was then digested with Sma I restriction enzyme for 2.5 hours under standard conditions to release the cloned glucanase inserts from their respective pArc vectors; digestion products were size fractionated on 1.2% agarose gels using avocado glucanase cDNA and tomato polygalacturonase cDNA clones as positive and negative controls, respectively. Following incubation in 250 mM HCl followed by 0.5 M NaOH/1.5M NaCl and finally by 0.5M Tris/3M NaCl gels were blotted to nitrocellulose and probed with each oligonucleotide probe end labeled as previously described. The largest glucanase insert was estimated to be 1.8 kilobases, similar to the previously characterized 1.9 kB avocado glucanase cDNA. This clone, termed pTCL1, was selected for sequencing.

3. Sequencing of tcl1 a. Subcloning

Sma I digestion of mini prep DNA prepared from the colonies described above released the 1.8 kB (estimated size) glucanase clone from the pArc vector. Digestion products were precipitated with 0.4 volumes ammonium acetate and 2 volumes ethanol and resuspended in 1×DNA sample buffer. Products were loaded onto a low-melt agarose gel with insert separated from vector by electrophoresis at 80 V. The insert was excised from the gel and stored as a gel slice at −20° C. until required. DNA concentration was estimated from the relative intensities of ethidium bromide staining between insert and defined standards.

Bluescript vector (SK+) (Stratagene Inc., La Jolla, Calif.) was linearized by Sma I digestion under standard conditions at 30° C. After 2.5 hours, digested vector was extracted once with phenol:chloroform:isoamyl alcohol (25:24:1) and once with chloroform-isoamyl alcohol (24:1) prior to precipitation with 0.4 volumes ammonium acetate and 2.5 volumes ethanol. The pelleted DNA was brought up in 500 ul 50 mM Tris, 0.1 mM EDTA, pH 8 and was dephosphorylated with Boehringer Mannheim calf intestine alkaline phosphatase as per the manufacturer's instructions for blunt ended DNA fragments. Dephosphorylated vector was harvested by ammonium acetate/EtOH precipitation as described previously and was brought to 100 ug/ml with water.

Dephosphorylated vector was ligated at 15° C. for 12 hours to melted glucanase insert from the low melt agarose gel. Ligation specifications were as follows for each 45 ul ligation: total DNA concentration =1 ug, insert:vector =2.1 on a molar basis. T4 DNA ligase =100 units/ml, final PEG concentration =5%.

Ligation mixtures were brought up to 100 ul with TE 8.0 and added to 200 ul freshly thawed XL1 Blue competent cells. After 30 minutes on ice, cells were heat shocked 5 minutes at 42° C. and added to 4 ml 2XL medium which had been prewarmed to 37° C. Cells were shaken at 100 rpm on an orbital shaker for 100 minutes at 37° C. and transferred to ice. Appropriate aliquots of the cells were then spread on LB agar plates containing 100 ug/ml ampicillin and 50 ug/ml tetracycline. Plates had been pre-spread with 100 ul of (50 ul 100 mM IPTG, 20 ul 20mg/ml X-gal, 30 ul LB). Plates were then incubated overnight at 37° C., at which time transformed colonies (white) could be distinguished from non-transformed colonies (blue). Miniprep DNA was isolated from transformants as previously described and digested with Sma I to release inserts. One glucanase transformant of approximately 1.8 kB was identified following the electrophoretic separation of digestion products on a 1.5% agarose gel. Double stranded miniprep DNA was prepared as previously described for sequencing purposes.

b. Sequencing

Double stranded DNA templates of varying lengths for use in first strand sequencing were generated by exonuclease digestion of glucanase miniprep DNA as described in the Erase-A-Base kit (Promega) protocol supplied by the manufacturer. Sequencing was conducted by the dideoxy method (Sanger, et al., *Proc Nat Acad Sci U.S.A.* 74:5463–5467) outlined fully in the Sequenase kit (United States Biochemical Co.) protocol provided by the manufacturer. Reverse M13 primer was purchased from Pharmacia.

Sequence data generated was entered and analyzed using the Microgenie sequence analysis computer program (Beckman Instruments, Inc.) strand resulted from the overlap of over 20 smaller sequences.

B. Vector Construction

Four different vectors were constructed. One vector, E8antiCL, contains the promoter from the tomato E8 gene and tcl1 antisense DNA. This promoter is inducible in ripening tomato fruit. The second vector, CaMVantiCL, contains the cauliflower mosaic virus 35S promoter and tcl1 antisense DNA. This promoter is constitutive. The other two vectors were constructed in the same manner but with the addition of polygalacturonase antisense DNA and appropriate promoters. The construction of the latter two vectors is illustrated in FIG. 1.

1. E8antiCL

A 2.0 kb E8 promoter fragment was isolated by cleaving pE8mutRN2.0 with Nco1. The preparation of pE8mutRN2.0 is described in Giovaninnoni et al., *The Plant Cell,* 1:53–63, 1989, which is incorporated herein by reference. The 5' overhang of the Nco1 restriction site was blunt-ended with the large fragment of DNA polymerase (Klenow fragment) and digested with EcoR1 restriction endonucleases. The resulting 2.0 kb EcoR1/filled Nco1 fragment was ligated into pUC118 cleaved with EcoR1 and Sma1 restriction endonucleases. The resulting construction, pE8mutRN2.0(+), retains the original Nco1 restriction site and includes BamH1, Xba1, Sal1, Pst1, Sph1, and Hind111 sites downstream of the Nco1 restriction site.

The 1.8 kb endo-1,4-β-glucanase cDNA cloned into the Sma1 site of the Bluescript M13+ (SK+) vector (Stratagene Inc., La Jolla, Calif.) was liberated by digestion with BamH1 and Kpn1 followed by agarose gel purification. The fragment was then ligated into BamH1/Kpn1 digested pUC118 to generate pUCCL1.8. The 1.8 kb BamH1/Sst1 cDNA insert of PUCCL1.8 was liberated by restriction endonuclease digestion and purified by agarose gel electrophoresis.

The resulting 1.8 kb BamH1/Sst1 fragment was utilized in a tri-molecular ligation with the 0.25 kb Sst1/EcoR1 Agrobacterium nopaline synthase gene transcription terminator fragment (capable of directing termination of gene transcription in plants) purified from pBI121 (Clonetech Inc., Palo Alto, Calif.) and ligated into pUC118 cleaved with BamH1 and EcoR1. The resulting pUCantiCL-ter construction contained the glucanase cDNA fused at its 5' end to the nopaline synthase gene transcription termination fragment via Sst1 site ligation. The 2.05 kb antiCL-ter fragment was isolated from pUCantiCL-ter by digestion with BamH1 followed by partial digestion with EcoR1. The 2.05 kb product was then purified on a agarose gel.

The resulting 2.05 kb EcoR1/BamH1 fragment was utilized in a tri-molecular ligation with the 2.0 kb EcoR1/BamH1 fragment purified from pE8mutRN2.0 and pUC118 cleaved with EcoR1. The resulting construction, pE8antiCL, contains the E8 promoter fused to the 3' end of the glucanase cDNA clone with the 5' end fused to the transcription termination fragment of the nopaline synthase gene. The internal EcoR1 site located between the cDNA and transcription terminator sequences was removed by partial digestion with EcoR1 restriction endonuclease followed by filling in of the EcoR1 5' overhang with Klenow enzyme and subsequent ligation of the filled in EcoR1 restriction endonuclease sites. The loss of the internal EcoR1 site was verified by restriction endonuclease mapping of the resulting construction, pE8antiCLR1. The 4.05 kb insert of pE8antiCL-R1 was liberated with EcoR1 restriction endonuclease, purified by agarose gel electrophoresis, and ligated into the EcoR1 site of the Agrobacterium T-DNA cointegrative shuttle vector pMLJ1, described in subsection 3, infra. The resulting construction is designated pMLJ1:E8antiCL.

2. CaMVantiCL

Regulatory sequences of the Cauliflower Mosaic Virus 35s transcription unit were isolated from pBI121 (Clonetech Inc., La Jolla, Calif.) by digestion with SphI and BamHI followed by agarose gel purification. The resulting 0.8 kb SphI/BamHI fragment was employed in a tri-molecular ligation with the 2.05 kb BamHI/EcoRI fragment of pUCantiCL-ter (described above) and pUC118 digested with Sph1 and EcoR1. The resulting construction was partially digested with EcoR1, and subjected to a fill-in reaction with Klenow enzyme followed by ligation to remove the internal EcoR1 restriction endonuclease site located between the 5' end of the cDNA and the plant transcription termination sequences. Restriction endonuclease mapping was employed to verify that the EcoR1 site between the cDNA and transcription termination sequences was removed. The resulting construction was designated pCaMVantiCL-S. pCaMVantiCL-S was digested with Sph1. The 3' overhang resulting from Sph1 digestion was filled in using T4 DNA polymerase and ligated to EcoR1 linkers (BRL, Bethesda, Md). The resulting construction was termed pCaMVantiCL. The 2.85 kb insert of pCaMVantiCL was isolated via digestion with EcoR1 restriction endonuclease followed by agarose gel purification and ligated into the EcoR1 site of pMLJ1 to generate pMLJ1: CaMVantiCL.

3. E8antiPG/CL

The 1.7 kb full length tomato fruit polygalacturonase cDNA insert of pBSPG1.9 (DellaPenna et al., *Plant Physiology* 90:1372-1377, 1989 which is incorporated herein by reference), cloned into the Sma1 site of the Bluescript M13+ (SK+) vector was liberated by digestion with Sal1 and Sst1 restriction endonucleases followed by agarose gel purification. The resulting 1.7 kb fragment was utilized in a tri-molecular ligation with the 0.25 kb Sst1/EcoR1 Agrobacterium nopaline synthase gene transcription termination sequence (described above) and Sal1/EcoR1 digested pUC118. The resulting construction was designated pUCantiPG-ter and consists of the 5' end of the polygalacturonase cDNA clone fused to the nopaline synthase transcription termination sequence at the Sst1 site.

The 1.95 kb insert of pUCantiPG-ter was liberated by digestion with Sal1 and EcoR1 restriction endonucleases followed by agarose gel purification. The resulting 1.95 kb Sal1/EcoR1 fragment was utilized in a tri-molecular ligation with the 2.0 kb EcoR1/Sal1 E8 promoter fragment isolated from pE8mutRN2.0(+) (described above) and pUCE8antiPG.

The 3.95 kb insert of pUCE8antiPG was isolated by agarose gel purification following digestion with EcoR1 restriction endonuclease and subsequent DNA polymerase (Klenow) fill-in of the 5' EcoR1 overhangs bordering both sides of the 3.95 kb antisense gene. The unique Sal1 restriction site of the cointegrative plant transformation vector, pMLJ1, was cleaved with Sal1 and filled in with Klenow enzyme. The blunt ended 3.95 kb E8antiPG fragment was ligated into the blunt ended Sal1 site of pMLJ1 to form pMIJ1:E8antiPG. pMLJ1:E8antiPG was cleaved in the unique EcoR1 site of the pMLJ1 sequences. The 4.05 kb insert of pE8antiCL-R1 (described above) was liberated with EcoR1 and purified by agarose gel electrophoresis. The resulting 4.05 kb E8antiCL-R1 fragment was ligated into the EcoR1 site of pMLJ1:E8antiPG to form pMLJ1:E8antiPG/CL (see FIG. 2).

4. CaMVantiPG/CL

Regulatory sequences of the Cauliflower Mosaic Virus 35S transcription unit were isolated from pBI121 as described above. The 1.95 kb insert of pUCantiPG-ter (described above) was isolated by digestion with EcoR1 and partial digestion with BamHI, followed by agarose gel purification of the resulting 1.95 kb fragment. The resulting 0.8 kb Sph1/BamH1 fragment of the CaMV 35S promoter was employed in a tri-molecular ligation with the 1.95 kb BamHI/EcoR1 insert of pUCantiPG-ter and pUC118 digested with Sph1 and EcoR1 restriction endonucleases to produce the construction designated pUCCaMVantiPG-S co. pUC-CaMVantiPG-S was digested with Sph1. The 3' overhang resulting from Sph1 digestion was filled in using T4 DNA polymerase and ligated to EcoR1 linkers (BRL, Bethesda, Md.). The resulting construction was termed pUCCaMVantiPG and contains the 2.75 kb CaMVantiPG gene cloned into the EcoR1 site of pUC118.

The 2.85 kb insert of pCaMVantiCL was isolated by agarose gel electrophoresis following digestion with EcoR1 restriction endonuclease and filling in of the 5' EcoR1 overhangs with Klenow enzyme. The unique Sal1 site of pMLJ1 was cleaved with Sal1 and filled in with Klenow enzyme. The 2.85 kb blunt end CaMVantiCL fragment was ligated into the EcoR1 site of pMLJ1:CaMVantiCL2 to form pMLJ1:CaMVantiPG/CL (see FIG. 2).

5. Co-integration of antisense gene constructions

Triparental mating was done according to methods well known in the art as described in Van Haute et al., *EMBO J.* 2:411–417, 1983, which is incorporated herein by reference. The shuttle vector used in the triparental mating is not a critical aspect of the invention. The particular shuttle vector used here, pMLJ1, is derived from that described in DeBloch et al., *EMBO J.* 3:1681–1689, 1984.

Triparental mating of *E. coli* (strain JM109) harboring pMLJ1:E8antiCL, pMLJ1:CaMVantiCL, pMLJ1:E8antiPG/CL, or pMLJ1:CamVantiPG/CL with *Agrobacterium tumefaciens* containing the cointegrative plant transformation vector pGV3850 (this vector is described in detail in Zambryski et al., *EMBO J.* 2:2143, 1983, which is incorporated herein by reference) and the helper *E. coli* strain pGJ23 resulted in cointegration of the antisense gene constructions into pGV3850, pGV3850:E8antiCL and pGV3850:CaMVantiCL were utilized to insert antisense endo-1,4-$\beta$-glucanase sequences into the tomato genome.

C. Transformation of Tomato With Antisense Endo-1,4-$\beta$-Glucanase Constructions

Summary of the Procedure

In brief, sterile cotyledon pieces were infected with Agrobacterium containing a Ti plasmid which includes within the T-DNA a neomycin phosphotransferase gene (NPT11) capable of conferring kanamycin resistance in transgenic plants. The co-integrative *Agrobacterium tumefaciens* Ti vector, pGV3850, with pMLJ1:E8antiCL, pMLJ1:CaMVantiCL, pMLJ1:E8antiPG/CL or pMLJ1:CamVantiPG/CL independently integrated into it, was used to transfer the two antisense gene constructions into independent tomato genomes. Co-cultivation of tomato (*Lycopersicon esculentum* cv Ailsa Craig) cotyledon pieces with the bacteria took place for 48 hours on tobacco feeder plates. The feeder cells increase the efficiency of transformation of tomato after the co-cultivation process. Regeneration of shoots was induced on the regeneration medium. From this stage on, antibiotics were used to inhibit the growth of Agrobacterium (Cefotaxime) and to select for transformed plant cells (kanamycin). Finally, shoots were transferred to rooting medium and then planted in soil and grown in the greenhouse.

1. Maintenance of feeder cells

To maintain the tobacco Xanthi suspension culture the cells were filtered through a 40 mesh filter once per week. 10 mls of filtrate were added to 100 mls of fresh Xanthi medium in a 500 ml flask.

2. Tomato seed germination

Approximately 50 seeds in a 50 ml beaker were stirred in 20 mls 70% EtOH for 2 minutes and rinsed with sterile water. They were then stirred 5 minutes in 20% bleach with 2 drops of Tween 80 and rinsed 4 times with sterile distilled $H_2O$.

Using sterile forceps, 12 to 15 seeds were placed on each plate. The petri plate was wrapper with parafilm and aluminum foil and grown at 25° C. After 5 days (when the seeds had reached about 60% germination), they were removed from the aluminum foil and grown under 2500 lux, with a 16 hour photoperiod. The seedlings were grown for a total of 8 days.

3. Preparation of feeder plates

Thick petri plates of approximately 40 mls of Xanthi suspension culture medium with 8 g/l agar were employed. 1 ml of a thick Xanthi suspension culture (7 days old) was pipetted onto each feeder plate. The plates were sealed with parafilm and incubated for 12 hours in the growth chamber (25° C.) on a lighted shelf.

4. Putting cotyledons on the feeder plates

A sterile Whatman #1 filter was placed onto each feeder cell plate. Cotyledons were cut with a scalpel in a drop of sterile water in a petri plate. The scalpel was rocked gently to make the cuts thus minimizing tearing and bruising of the tissue. Only the ends of the cotyledons were cut off. Cut cotyledons were placed onto the filter paper on the feeder plate upside-down (cuticle side down). Approximately 50 cotyledon pieces were placed on each plate. The plates were sealed with parafilm and placed in the growth chamber for 16 hours.

5. Infection with Transformed Agrobacterium 10 ml overnight cultures of the Agrobacterium containing pMLJ1:E8antiCL and pMLJ1:CaMVantiCL were grown in YE8 medium supplemented with 25 ug/ml spectinomycin. Agrobacterium overnight cultures were diluted four-fold in the seed germination medium to an O. D. of 590. 0.5 mls of diluted bacteria were aliquoted into a petri dish followed by addition 30 cotyledon pieces previously co-cultivated with tobacco feeder cells. The Agrobacterium/cotyledon mixture was swirled to wet. The cotyledons were wet in the bacteria for 5 minutes. The cotyledons were touched once to a sterile paper towel. Cotyledons were placed back on the same feeder plates upside-down and co-cultivated for an additional 48 hours.

6. Regeneration

After co-cultivation with the bacteria, cotyledons were placed on the regeneration medium right-side-up. The edges of the cotyledon will curl down into the agar insuring the wounded surfaces will be in direct contact with the drugs. 15 cotyledon pieces were placed on each plate.

Within 10 days callus was visible at the edges of the infected cotyledons. Cotyledon pieces were transferred to fresh plates every 2 weeks. Shoots and dark green callus was transferred to shooting medium (same as regeneration medium except that the zeatin concentration is reduced to 0.1 mg/ml). After 6 weeks (3 transfers) all callus and shoots were transferred to shooting medium.

For rooting, TM5 rooting medium was employed. (Shahin, Theor. Appl. Gen. 69: 235–240, 1985). The levels of kanamycin and cefatoxime are reduced to 25 mg/l and 125 mg/l, respectively.

After the shoots developed sufficient roots, they were transferred to soil. To transfer plants to soil, they were gently removed from the agar using a spatula to scrape away most of the agar. The roots were rinsed in warm water to remove as much agar as possible. They were planted in clay pots which were placed inside GA-7 boxes. The covers of the boxes were gradually opened over several days and watered with ½-strength Hoagland's solution every other watering. After 2 weeks, the plants were completely uncovered in the growth chamber and were transplanted into large pots and moved to the greenhouse.

7. Media a. Xanthi Suspension Culture Medium

|  |  | stock |
|---|---|---|
| 1 bottle KC MS Salts (MM100) | 4.3 g |  |
| i-inositol | 100 mg |  |
| sucrose | 30 g |  |
| KH₂PO4 | 2 mls | 100 mg/ml |
| thiamine | 1.3 mls | 1 mg/ml |
| 2,4-D | 2 mls | 100 mg/l |
| kinetin | 0.4 mls | 0.25 mg/ml |
| pH 5.5 with KOH |  |  |
| H₂O to 1 liter |  |  |
| aliquot 100 mls into 500 ml flasks |  |  |
| plug the flasks and cap with aluminum foil |  |  |
| autoclave 20' |  |  | b. Plates for seed germination

| MS Medium | 1 pkg. KC MM-100 |
|---|---|
| 3% sucrose | 30 g sucrose |
|  | 800 mls H₂O |
| pH to 5.7 with KOH |  |
| volume to 1 liter |  |
| add 8 g bacto agar (0.8% agar) |  |
| autoclaved 20 minutes |  |
| poured into thick petri plates (about 30 mls per plate) |  | c. Regeneration medium for 1 liter:

4.3 g MS salts (KC MM-100)
30 g glucose
0.59 g MES
2 ml 500×Gamborgs vitamins (see below)
ph to 5.8 with 1N KOH
Volume to 1 liter
8 g tissue culture grade agar
Autoclave 20 minutes
Cool to 50 degrees C.
Add:
   1 mg sterile zeatin (trans-isomer)
   300 mg/l cefotaxime (Calbiochem Cat #219380)
   50 mg/l kanamycin
   500×Gamborgs vitamins:
   5 g myo-inositol
   0.5 g thiamine HCL
   50 mg nicotinic acid
   50 mg pyridoxine HCl
   100 ml sterile water Cefotaxime is light sensitive. It turns yellow when it's been in the light for too long. So plates containing Cefotaxime were made the day before use.

d. TM5 for root induction

| Ingredient | amount/liter |
|---|---|
| MS salts | 4.3 g |
| Potato vitamins (200×) | 5 mls |
| Sucrose | 30 g |
| IBA (indole-3-butyric acid, Sigma) | 0.1 mg (add before autoclaving) |
| Purified agar | 7 g |
| adjust pH to 5.8 with KOH |  |
| Autoclave 15 minutes. |  |

When cooled to 50° C. add 25 mg kanamycin and 125 mg cefotaxime.

| Potato vitamins (200×) | |
|---|---|
| Ingredient | amount/liter |
| myo-inositol | 20 g |
| thiamine-HCl | 100 mg |
| pyridoxine-HCl | 100 mg |
| nicotinic acid | 1 g |
| glycine | 500 mg |
| biotin | 10 mg |
| folic acid | 100 mg |
| adjust pH to 5.8 to 6.0 to clear solution. | |
| Store at −20° C. | |

---

What is claimed is:

1. An expression cassette comprising a plant promoter sequence operably linked to a DNA subsequence of at least 20 base pairs derived from a DNA sequence encoding tomato a endo-1,4-β-glucanase, the DNA subsequence being linked to the promoter sequence in the opposite orientation for expression.

2. An expression cassette as in claim 1 wherein the promoter is inducible.

3. An expression cassette as in claim 1 wherein the promoter is derived from a tomato E8 gene.

4. An expression cassette as in claim 1 wherein the promoter is constitutive.

5. An expression cassette as in claim 1 wherein the promoter is derived from cauliflower mosaic virus.

6. An expression cassette as in claim 1 wherein the DNA sequence encoding tomato endo-1,4-β-glucanase is SEQ. ID. No. 1.

7. An expression cassette as in claim 1 wherein the DNA sequence encoding tomato endo-1,4-β-glucanase comprises SEQ. ID. No. 3.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1718 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: CDS
    ( B ) LOCATION: 70..1572

( x i ) SEQUENCE DESCRIPTION: SEQ ID NO:1:

```
ATAAACATAA TATTAAATAG TCATAAACCA TATGTTAAAT AATAATAATA ATTAATTAAT        60

AATAACAAT ATG GCT TGT TCA AAG AAT ATT TGG GTT ATT GTT ATA TTC          108
          Met Ala Cys Ser Lys Asn Ile Trp Val Ile Val Ile Phe
            1               5                  10

TTT TTG TGC ATT TTG GCT GGT CCT ATT ATT GCT CAA GAT TAC AAT GAT        156
Phe Leu Cys Ile Leu Ala Gly Pro Ile Ile Ala Gln Asp Tyr Asn Asp
     15              20                  25

TCA CTT GGC AAA GCT ATT TTA TTC TTT GAA GGG CAA CGT TCT GGA AAA        204
Ser Leu Gly Lys Ala Ile Leu Phe Phe Glu Gly Gln Arg Ser Gly Lys
 30              35                  40                  45

TTA CCA GTT TCT CAA AGA GTC AAA TGG AGA GGA GAT TCC GCA CTC ATC        252
Leu Pro Val Ser Gln Arg Val Lys Trp Arg Gly Asp Ser Ala Leu Ile
             50                  55                  60

GAT GGC ATA ATT GAA CAT GTG AAT TTG ATT GGA GGC TAC TAT GAT GCT        300
Asp Gly Ile Ile Glu His Val Asn Leu Ile Gly Gly Tyr Tyr Asp Ala
                 65                  70                  75

GGT GAC AAT GTA AAA TTT GGA TGG CCC ATG GCT TAT TCT TTA ACC TTG        348
Gly Asp Asn Val Lys Phe Gly Trp Pro Met Ala Tyr Ser Leu Thr Leu
             80                  85                  90

TTG AGT TGG GCT GCT ATT GAA TAT CAA ACA CAA ATC TCT TCA ACA AAT        396
Leu Ser Trp Ala Ala Ile Glu Tyr Gln Thr Gln Ile Ser Ser Thr Asn
 95                 100                 105

CAA CTT GTA CAC CTC CAA AAT GCA ATT CGT TGG GGC ACA AAT TTC TTA        444
Gln Leu Val His Leu Gln Asn Ala Ile Arg Trp Gly Thr Asn Phe Leu
110                 115                 120                 125

ATT CGA GCC CAT ACT TCA AGT ACA ACT CTC TAT ACT CAG GTT GGA GAT     492
   Ile Arg Ala His Thr Ser Ser Thr Thr Leu Tyr Thr Gln Val Gly Asp
                   130                 135                 140

GGA AAT GCA GAT CAC CAA TGT TGG GAA AGA CCA GAA GAC ATG GAT ACT        540
Gly Asn Ala Asp His Gln Cys Trp Glu Arg Pro Glu Asp Met Asp Thr
                145                 150                 155

CCT AGA ACA CTA TAT AAA ATA ACA TCA AAT TCT CCA GGA TCT GAG GTG        588
Pro Arg Thr Leu Tyr Lys Ile Thr Ser Asn Ser Pro Gly Ser Glu Val
            160                 165                 170

GCA GCT GAC GTG GCA GCT GCT TTT GCT GCT GCT TCA ATA GTT TTC AAA        636
Ala Ala Asp Val Ala Ala Ala Phe Ala Ala Ala Ser Ile Val Phe Lys
        175                 180                 185

AAT ATT GAT TCC AAC TAT TCT ACA AAG TTA TTA AAA AGA TCA AGA TCC        684
Asn Ile Asp Ser Asn Tyr Ser Thr Lys Leu Leu Lys Arg Ser Arg Ser
190                 195                 200                 205

TTA TTT GCA TTT GCG GAT AAG TAT AGA GGA TCT TAC CAA GCT TCT TGT        732
Leu Phe Ala Phe Ala Asp Lys Tyr Arg Gly Ser Tyr Gln Ala Ser Cys
            210                 215                 220

CCA TTC TAT TGT TCC TAC TCA GGT TAT AAG GAT GAA TTG TTG TGG GCT        780
Pro Phe Tyr Cys Ser Tyr Ser Gly Tyr Lys Asp Glu Leu Leu Trp Ala
                225                 230                 235

GCT GCT TGG CTA TAT AAG GCA GGT GGA GGA AAC AAT TAT TTA AAT TAT        828
Ala Ala Trp Leu Tyr Lys Ala Gly Gly Gly Asn Asn Tyr Leu Asn Tyr
            240                 245                 250

GCT TCA ATC AAC CAA GGT TGG AGT CAA GTT GCC TCT GAG TTT AGT TGG        876
Ala Ser Ile Asn Gln Gly Trp Ser Gln Val Ala Ser Glu Phe Ser Trp
        255                 260                 265

GAT GAC AAG TTT GCT GGA GCC CAA ACT TTA CTA GCT AAG GAA TAC CTT        924
Asp Asp Lys Phe Ala Gly Ala Gln Thr Leu Leu Ala Lys Glu Tyr Leu
270                 275                 280                 285
```

| | | | | | | | | | | | | | | | | |
|---|---|---|---|---|---|---|---|---|---|---|---|---|---|---|---|---|
| AAT | GGA | AAG | AGC | AAT | TTG | GAA | AAA | TTC | AAG | AAA | GAT | GCT | GAT | TCA | TTT | 972 |
| Asn | Gly | Lys | Ser | Asn | Leu | Glu | Lys | Phe | Lys | Lys | Asp | Ala | Asp | Ser | Phe | |
| | | | 290 | | | | | 295 | | | | | 300 | | | |
| ATT | TGT | GGA | TTA | ATG | CCA | GAA | AGT | AGC | TCT | ATA | CAA | ATT | AAG | ACA | ACC | 1020 |
| Ile | Cys | Gly | Leu | Met | Pro | Glu | Ser | Ser | Ser | Ile | Gln | Ile | Lys | Thr | Thr | |
| | | | | 305 | | | | | 310 | | | | | 315 | | |
| CCA | GGT | GGA | CTT | TTG | TAT | TAT | AGA | GAT | AGT | AGC | AAT | TTG | CAA | TAT | GTG | 1068 |
| Pro | Gly | Gly | Leu | Leu | Tyr | Tyr | Arg | Asp | Ser | Ser | Asn | Leu | Gln | Tyr | Val | |
| | | | 320 | | | | | 325 | | | | | 330 | | | |
| AAT | GGT | GCC | ACT | ATG | GTA | CTT | TTT | ATG | TAC | ACT | AAA | GTC | CTT | GAG | GCA | 1116 |
| Asn | Gly | Ala | Thr | Met | Val | Leu | Phe | Met | Tyr | Thr | Lys | Val | Leu | Glu | Ala | |
| | | 335 | | | | | 340 | | | | | 345 | | | | |
| GCT | GGA | ATA | GGA | GGA | GTT | ACA | TGT | GGA | TCT | GTT | AAT | TTT | TCC | ACA | TCC | 1164 |
| Ala | Gly | Ile | Gly | Gly | Val | Thr | Cys | Gly | Ser | Val | Asn | Phe | Ser | Thr | Ser | |
| 350 | | | | | 355 | | | | | 360 | | | | | 365 | |
| AAG | ATT | AAA | GCC | TTT | GCA | AAA | TTA | CAG | GTT | GAC | TAC | ATA | CTT | GGA | AAC | 1212 |
| Lys | Ile | Lys | Ala | Phe | Ala | Lys | Leu | Gln | Val | Asp | Tyr | Ile | Leu | Gly | Asn | |
| | | | | 370 | | | | | 375 | | | | | 380 | | |
| AAT | CCA | CTC | AAA | ATG | TCA | TAC | ATG | GTG | GGA | TTT | GGC | AAC | AAA | TAT | CCA | 1260 |
| Asn | Pro | Leu | Lys | Met | Ser | Tyr | Met | Val | Gly | Phe | Gly | Asn | Lys | Tyr | Pro | |
| | | | 385 | | | | | 390 | | | | | 395 | | | |
| ACA | AAA | CTT | CAC | CAT | AGA | GCC | TCA | TCA | CTC | CCT | TCA | ATT | TAT | AAC | CAT | 1308 |
| Thr | Lys | Leu | His | His | Arg | Ala | Ser | Ser | Leu | Pro | Ser | Ile | Tyr | Asn | His | |
| | | | 400 | | | | | 405 | | | | | 410 | | | |
| CCA | ACT | AGG | GTG | GGG | TGC | AAC | GAT | GGC | TAT | AGT | TCA | TGG | TAC | AAT | TCT | 1356 |
| Pro | Thr | Arg | Val | Gly | Cys | Asn | Asp | Gly | Tyr | Ser | Ser | Trp | Tyr | Asn | Ser | |
| | | 415 | | | | | 420 | | | | | 425 | | | | |
| AAC | AAT | CCA | AAC | CCT | AAC | ACA | CAT | GTC | GGT | GCG | ATC | GTC | GGT | GGG | CCT | 1404 |
| Asn | Asn | Pro | Asn | Pro | Asn | Thr | His | Val | Gly | Ala | Ile | Val | Gly | Gly | Pro | |
| 430 | | | | | 435 | | | | | 440 | | | | | 445 | |
| AAT | TCC | GGG | GAC | CAA | TTT | ATT | GAT | TCG | CGA | TCA | GAT | TAC | TCT | CAT | TCT | 1452 |
| Asn | Ser | Gly | Asp | Gln | Phe | Ile | Asp | Ser | Arg | Ser | Asp | Tyr | Ser | His | Ser | |
| | | | | 450 | | | | | 455 | | | | | 460 | | |
| GAA | CCC | ACG | ACT | TAT | ATG | AAT | GCA | GCA | TTT | ATA | GGG | TCC | GTG | GCC | GCT | 1500 |
| Glu | Pro | Thr | Thr | Tyr | Met | Asn | Ala | Ala | Phe | Ile | Gly | Ser | Val | Ala | Ala | |
| | | | 465 | | | | | 470 | | | | | 475 | | | |
| TTG | ATT | GAT | CAA | ACC | AAA | GAA | GGA | GAA | CAC | TAT | GGG | GAA | ATT | AAT | TCA | 1548 |
| Leu | Ile | Asp | Gln | Thr | Lys | Glu | Gly | Glu | His | Tyr | Gly | Glu | Ile | Asn | Ser | |
| | | 480 | | | | | 485 | | | | | 490 | | | | |
| CAA | TTT | AAC | AAA | ACA | GGT | TTT | ATG | TAGTAGATAA | ATTAGTAAAG | AAGT | | | | | | 1596 |
| Gln | Phe | Asn | Lys | Thr | Gly | Phe | Met | | | | | | | | | |
| | 495 | | | | | 500 | | | | | | | | | | |

GAATGTCATG CAATTATTGA TAAATATATG TACATATAAT GAATTATCAT AAATGTATGA      1656

AGCTATAAAT ATTACATAAT AGAAATAAAT AAATATCAAA AATGTATCTT TTTTTTTTTT     1716

TT                                                                    1718

( 2 ) INFORMATION FOR SEQ ID NO:2:

( i ) SEQUENCE CHARACTERISTICS:
        ( A ) LENGTH: 501 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ala | Cys | Ser | Lys | Asn | Ile | Trp | Val | Ile | Val | Ile | Phe | Phe | Leu | Cys |
|---|---|---|---|---|---|---|---|---|---|---|---|---|---|---|---|
| 1 | | | | 5 | | | | | 10 | | | | | 15 | |

| Ile | Leu | Ala | Gly | Pro | Ile | Ile | Ala | Gln | Asp | Tyr | Asn | Asp | Ser | Leu | Gly |
|---|---|---|---|---|---|---|---|---|---|---|---|---|---|---|---|
| | | | | 20 | | | | | 25 | | | | | 30 | |

| Lys | Ala | Ile | Leu | Phe | Phe | Glu | Gly | Gln | Arg | Ser | Gly | Lys | Leu | Pro | Val |
|---|---|---|---|---|---|---|---|---|---|---|---|---|---|---|---|
| | | | 35 | | | | | 40 | | | | | 45 | | |

```
Ser Gln Arg Val Lys Trp Arg Gly Asp Ser Ala Leu Ile Asp Gly Ile
    50                  55                  60
Ile Glu His Val Asn Leu Ile Gly Gly Tyr Tyr Asp Ala Gly Asp Asn
65                  70                  75                  80
Val Lys Phe Gly Trp Pro Met Ala Tyr Ser Leu Thr Leu Leu Ser Trp
                85                  90                  95
Ala Ala Ile Glu Tyr Gln Thr Gln Ile Ser Ser Thr Asn Gln Leu Val
            100                 105                 110
His Leu Gln Asn Ala Ile Arg Trp Gly Thr Asn Phe Leu Ile Arg Ala
        115                 120                 125
His Thr Ser Ser Thr Thr Leu Tyr Thr Gln Val Gly Asp Gly Asn Ala
    130                 135                 140
Asp His Gln Cys Trp Glu Arg Pro Glu Asp Met Asp Thr Pro Arg Thr
145                 150                 155                 160
Leu Tyr Lys Ile Thr Ser Asn Ser Pro Gly Ser Glu Val Ala Ala Asp
                165                 170                 175
Val Ala Ala Ala Phe Ala Ala Ala Ser Ile Val Phe Lys Asn Ile Asp
            180                 185                 190
Ser Asn Tyr Ser Thr Lys Leu Leu Lys Arg Ser Arg Ser Leu Phe Ala
        195                 200                 205
Phe Ala Asp Lys Tyr Arg Gly Ser Tyr Gln Ala Ser Cys Pro Phe Tyr
    210                 215                 220
Cys Ser Tyr Ser Gly Tyr Lys Asp Glu Leu Leu Trp Ala Ala Ala Trp
225                 230                 235                 240
Leu Tyr Lys Ala Gly Gly Gly Asn Asn Tyr Leu Asn Tyr Ala Ser Ile
                245                 250                 255
Asn Gln Gly Trp Ser Gln Val Ala Ser Glu Phe Ser Trp Asp Asp Lys
            260                 265                 270
Phe Ala Gly Ala Gln Thr Leu Leu Ala Lys Glu Tyr Leu Asn Gly Lys
        275                 280                 285
Ser Asn Leu Glu Lys Phe Lys Lys Asp Ala Asp Ser Phe Ile Cys Gly
    290                 295                 300
Leu Met Pro Glu Ser Ser Ser Ile Gln Ile Lys Thr Thr Pro Gly Gly
305                 310                 315                 320
Leu Leu Tyr Tyr Arg Asp Ser Ser Asn Leu Gln Tyr Val Asn Gly Ala
                325                 330                 335
Thr Met Val Leu Phe Met Tyr Thr Lys Val Leu Glu Ala Ala Gly Ile
            340                 345                 350
Gly Gly Val Thr Cys Gly Ser Val Asn Phe Ser Thr Ser Lys Ile Lys
        355                 360                 365
Ala Phe Ala Lys Leu Gln Val Asp Tyr Ile Leu Gly Asn Asn Pro Leu
    370                 375                 380
Lys Met Ser Tyr Met Val Gly Phe Gly Asn Lys Tyr Pro Thr Lys Leu
385                 390                 395                 400
His His Arg Ala Ser Ser Leu Pro Ser Ile Tyr Asn His Pro Thr Arg
                405                 410                 415
Val Gly Cys Asn Asp Gly Tyr Ser Ser Trp Tyr Asn Ser Asn Asn Pro
            420                 425                 430
Asn Pro Asn Thr His Val Gly Ala Ile Val Gly Gly Pro Asn Ser Gly
        435                 440                 445
Asp Gln Phe Ile Asp Ser Arg Ser Asp Tyr Ser His Ser Glu Pro Thr
    450                 455                 460
Thr Tyr Met Asn Ala Ala Phe Ile Gly Ser Val Ala Ala Leu Ile Asp
465                 470                 475                 480
```

```
Gln  Thr  Lys  Glu  Gly  Glu  His  Tyr  Gly  Glu  Ile  Asn  Ser  Gln  Phe  Asn
               485                      490                      495

Lys  Thr  Gly  Phe  Met
                    500
```

(2) INFORMATION FOR SEQ ID NO:3:

(i) SEQUENCE CHARACTERISTICS:
        (A) LENGTH: 205 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..204

(xi) SEQUENCE DESCRIPTION: SEQ ID NO:3:

```
GTT  TTT  CCG  ATG  GCG  TTT  ACG  ACG  ACA  TTG  TTA  TCG  TGG  AGT  ATA  ATT       48
Val  Phe  Pro  Met  Ala  Phe  Thr  Thr  Thr  Leu  Leu  Ser  Trp  Ser  Ile  Ile
  1                 5                        10                      15

GAT  TTT  AAA  AGG  AAT  ATA  GGG  AAT  GAA  TTG  GGT  AAT  GCA  GTG  AAG  GCG       96
Asp  Phe  Lys  Arg  Asn  Ile  Gly  Asn  Glu  Leu  Gly  Asn  Ala  Val  Lys  Ala
                    20                  25                       30

GTG  AAA  TGG  GGA  ACT  GAT  TTT  CTG  TTG  AAA  GCT  ACG  GCG  AGA  GAT  GGA      144
Val  Lys  Trp  Gly  Thr  Asp  Phe  Leu  Leu  Lys  Ala  Thr  Ala  Arg  Asp  Gly
               35                       40                  45

GTG  ATA  TAT  GTA  CAA  GTT  GGT  GAT  GCG  TTT  TCA  GAT  CAC  AGT  TGT  TGG      192
Val  Ile  Tyr  Val  Gln  Val  Gly  Asp  Ala  Phe  Ser  Asp  His  Ser  Cys  Trp
     50                       55                       60

GAG  AGA  CCA  GAG  A                                                                205
Glu  Arg  Pro  Glu
 65
```

(2) INFORMATION FOR SEQ ID NO:4:

(i) SEQUENCE CHARACTERISTICS:
        (A) LENGTH: 68 amino acids
        (B) TYPE: amino acid
        (D) TOPOLOGY: linear (ii) MOLECULE TYPE: protein (xi) SEQUENCE DESCRIPTION: SEQ ID NO:4:

```
Val  Phe  Pro  Met  Ala  Phe  Thr  Thr  Thr  Leu  Leu  Ser  Trp  Ser  Ile  Ile
  1                 5                        10                      15

Asp  Phe  Lys  Arg  Asn  Ile  Gly  Asn  Glu  Leu  Gly  Asn  Ala  Val  Lys  Ala
                    20                  25                       30

Val  Lys  Trp  Gly  Thr  Asp  Phe  Leu  Leu  Lys  Ala  Thr  Ala  Arg  Asp  Gly
               35                       40                  45

Val  Ile  Tyr  Val  Gln  Val  Gly  Asp  Ala  Phe  Ser  Asp  His  Ser  Cys  Trp
     50                       55                       60

Glu  Arg  Pro  Glu
 65
```